United States Patent
Hsu et al.

(10) Patent No.: US 11,547,546 B2
(45) Date of Patent: Jan. 10, 2023

(54) SYSTEM AND METHOD FOR INCREASING A CROSS-SECTIONAL AREA OF A BODY LUMEN

(71) Applicant: Prodeon, Inc., Taipei (TW)

(72) Inventors: Thomas Hsu, Foster City, CA (US); Senzan Hsu, Foster City, CA (US); Ellen Hsu, Foster City, CA (US)

(73) Assignee: Prodeon Medical Corporation, Taipei (TW)

( * ) Notice: Subject to any disclaimer, the term of this patent is extended or adjusted under 35 U.S.C. 154(b) by 946 days.

(21) Appl. No.: 16/065,344

(22) PCT Filed: Dec. 22, 2016

(86) PCT No.: PCT/US2016/068272
§ 371 (c)(1),
(2) Date: Jun. 22, 2018

(87) PCT Pub. No.: WO2017/112856
PCT Pub. Date: Jun. 29, 2017

(65) Prior Publication Data
US 2021/0205064 A1    Jul. 8, 2021

Related U.S. Application Data

(60) Provisional application No. 62/392,388, filed on May 31, 2016, provisional application No. 62/387,090, filed on Dec. 22, 2015.

(51) Int. Cl.
*A61F 2/04* (2013.01)
*A61B 90/00* (2016.01)

(52) U.S. Cl.
CPC ............... *A61F 2/04* (2013.01); *A61B 90/02* (2016.02); *A61F 2002/047* (2013.01);
(Continued)

(58) Field of Classification Search
CPC .............. A61F 2/04; A61F 2002/047; A61F 2220/0016; A61F 2250/0065;
(Continued)

(56) References Cited

U.S. PATENT DOCUMENTS 5,882,353 A    3/1999  Vanbeek et al.
6,197,030 B1 *  3/2001  Pham .................. A61B 17/688
                                                606/323
(Continued)

FOREIGN PATENT DOCUMENTS

CN    101208060 A    6/2008
CN    201353367 Y   12/2009
(Continued)

OTHER PUBLICATIONS

International Search Report and Written Opinion for corresponding PCT Appln No. PCT/US16/68272, dated Mar. 30, 2017.
(Continued)

*Primary Examiner* — Yashita Sharma
(74) *Attorney, Agent, or Firm* — Dergosits & Noah LLP; Todd A. Noah

(57) ABSTRACT

Devices and methods are disclosed for managing and/or treating body tissues obstructing a hollow body lumen, such as the prostatic lobe tissues obstructing the urethra. A scaffolding may be provided with opposing tissue-engaging portions and at least one expansion member configured to transition between a compressed configuration having a reduced distance between the tissue-engaging portions and a deployed configuration having an increased distance between the tissue-engaging portions.

11 Claims, 13 Drawing Sheets

(52) U.S. Cl.
CPC .......... *A61F 2220/0016* (2013.01); *A61F 2250/0065* (2013.01); *A61F 2250/0068* (2013.01)

(58) Field of Classification Search
CPC ...... A61F 2250/0068; A61F 2002/8483; A61F 2002/8486; A61F 2/848; A61F 2220/0091; A61F 2250/0031; A61F 2250/0067; A61F 2/00; A61B 90/02; A61B 1/00087
See application file for complete search history.

(56) References Cited

U.S. PATENT DOCUMENTS

| | | | |
|---|---|---|---|
| 6,917,030 | B2 | 7/2005 | Knee et al. |
| 2002/0138097 | A1 | 9/2002 | Ostrovsky et al. |
| 2003/0014101 | A1 | 1/2003 | Harrison |
| 2004/0147953 | A1 | 7/2004 | Gedebou |
| 2005/0203534 | A1* | 9/2005 | Mommaerts ......... A61B 17/663 606/90 |
| 2007/0016163 | A1 | 1/2007 | Santini et al. |
| 2008/0125757 | A1 | 5/2008 | Gobel |
| 2009/0306681 | A1 | 12/2009 | Del Nido et al. |
| 2010/0049244 | A1 | 2/2010 | Cohen et al. |
| 2010/0222802 | A1 | 9/2010 | Gillespie, Jr. et al. |
| 2011/0251691 | A1 | 10/2011 | McLaughlin et al. |
| 2012/0035608 | A1 | 2/2012 | Marchitto et al. |
| 2012/0265133 | A1 | 10/2012 | Ostrovsky et al. |
| 2015/0257908 | A1 | 9/2015 | Mehta et al. |

FOREIGN PATENT DOCUMENTS

| | | |
|---|---|---|
| JP | 2013-523406 A | 6/2013 |
| JP | 2017507752 A | 3/2017 |
| WO | 1995026696 | 10/1995 |
| WO | 2007000756 A2 | 1/2007 |
| WO | 2007040949 A2 | 4/2007 |
| WO | 2010068467 A1 | 6/2010 |
| WO | 2011130329 A | 10/2011 |

OTHER PUBLICATIONS

Office Action from corresponding Chinese Patent Application No. 201680082395 dated May 8, 2021.

Office Action from corresponding Chinese Patent Application No. 201680082395 dated Jul. 3, 2020.

Search Report from corresponding European Patent Application No. 16880087.8 dated Jul. 24, 2019.

Search Report from corresponding Japanese Patent Application No. 2018-533793, dated Sep. 25, 2020.

* cited by examiner

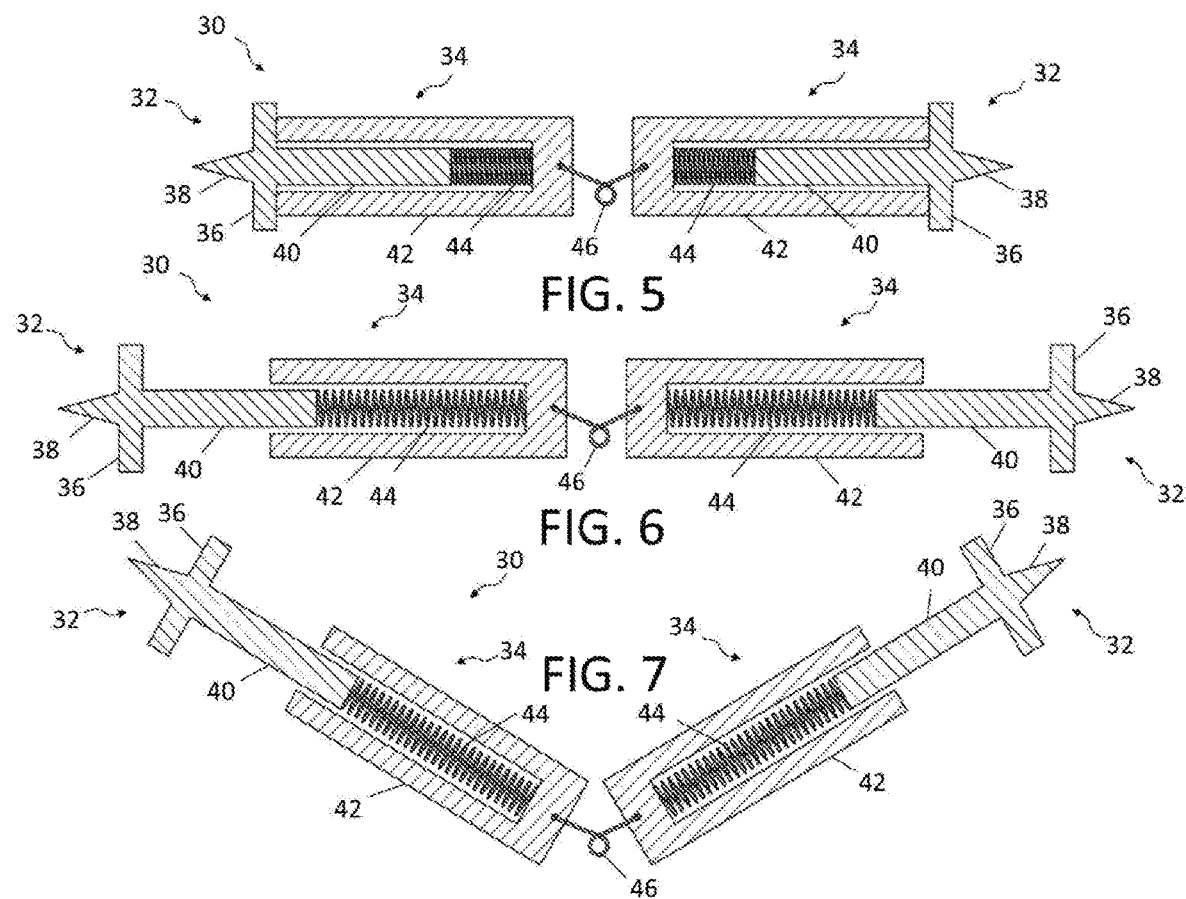
FIG. 5
FIG. 6
FIG. 7
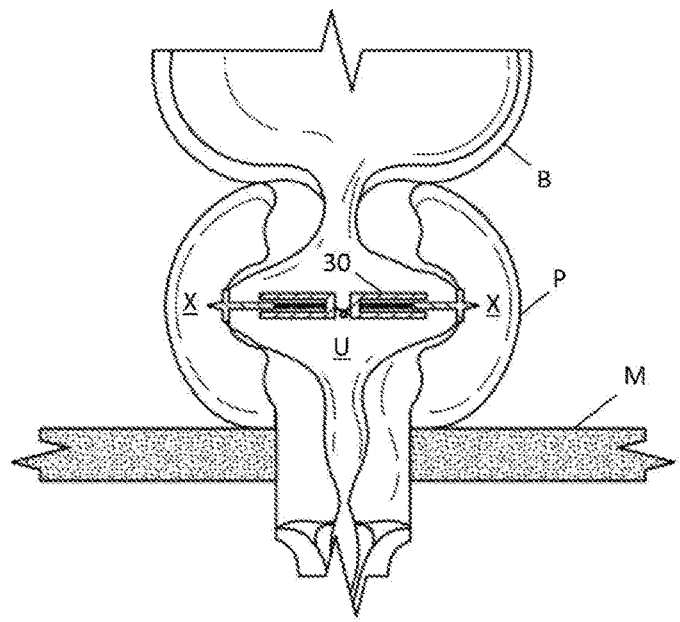
FIG. 8

SYSTEM AND METHOD FOR INCREASING A CROSS-SECTIONAL AREA OF A BODY LUMEN

RELATED APPLICATIONS

This application claims the benefit of U.S. Provisional Patent Application No. 62/387,090 filed Dec. 22, 2015 and U.S. Provisional Patent Application No. 62/392,388 filed May 31, 2016, the disclosures of which are incorporated by reference in their entirety.

FIELD OF THE PRESENT DISCLOSURE

The invention relates to devices and methods managing or treating body tissues obstructing a hollow body lumen, such as the prostatic lobe tissues obstructing the urethra.

BACKGROUND

Benign prostatic hyperplasia (BPH) is a common disease that affects 50-60% of men over age 50 and 80-90% of men over age 70. Oral medications have been used as the first-line therapy in the U.S. and many European nations. However, prostate size generally continues to increase with time in most men, leading to further urethral obstruction. Correspondingly, procedural intervention usually becomes necessary at some point during the pharmacologic management of BPH. Current procedural intervention includes transurethral resection of the prostate and targeted removal of tissue by the application of directed energy, such as ablation with laser, microwave or radio frequency energy or other vaporization techniques. However, such procedures which have been associated with complications such as bladder neck contracture, impotence, retrograde ejaculation and others. In addition, most of these procedures require general or regional anesthesia use and may require hospitalization. As a less-invasive alternative, the use of long-term urethral stents for management of BPH has been attempted but has been found to suffer from encrustation and pose difficulty in removal, making the practice unpopular among urologists. Other alternatives such as an indwelling urinary catheter or intermittent self-catheterization have been associated with significant patient discomfort and inconvenience, as well as raising the risk of urinary tract infection and hematuria. Thus, such techniques may be considered unappealing to many patients and are generally unsuitable for long-term BPH management. As a consequence, patients may have a difficult time in deciding among the conventional choices of procedural management. Furthermore, many patients may experience an overactive bladder and/or exhibit clinical voiding symptoms that are not clearly consistent with BPH, making the diagnosis of BPH (and subsequent management) challenging to the urologists. With the lack of suitable treatment options, elaborate urodynamic evaluation or testing may often be necessary.

In view of the above, it would be desirable to provide devices and methods that provide adequate management of BPH without the complications and problems of the current procedural modalities noted above, including the removal of the obstructing prostate tissues, the placement of stents, the use of an indwelling urinary catheter or intermittent self-catheterization. Likewise, it would be desirable to provide management of BPH in an outpatient or office-based setting while reducing the need for anesthesia. Further, it would be desirable to provide techniques for managing BPH with reversible clinical effects. Still further, it would be desirable to provide BPH management in clinically challenging diagnostic situations without the need for elaborate urodynamic evaluation. The present disclosure details methods and devices that satisfy these and other needs, as well as being simple and inexpensive to manufacture, simple to use and robust in use, and that be used with a variety of hollow body structures such as the pro static urethra to restore or increase patency.

SUMMARY

This disclosure includes a device for increasing a cross-sectional area of a body lumen. The device may be scaffolding with opposing tissue-engaging portions and at least one expansion member configured to transition between a compressed configuration having a reduced distance between the tissue-engaging portions and a deployed configuration having an increased distance between the tissue-engaging portions.

In one aspect, the tissue-engaging portions may be a lateral plate. The tissue-engaging portions may also have an anchor.

In one aspect, at least one of the expansion members may be telescoping.

In one aspect, the at least one expansion member may be a bi-directional expansion member, such that the tissue-engaging portions are secured to opposing ends of the bi-directional expansion member.

In one aspect, a pair of uni-directional expansion members may be coupled in opposing directions, such that each tissue-engaging portion is secured to one end of each uni-directional expansion member. The pair of uni-directional expansion members may be coupled by a pivot, wherein the pivot is biased to align the uni-directional expansion members longitudinally but allows the uni-directional expansion members to deflect with respect to each other. A tether may be secured to the pivot.

In one aspect, at least a portion of the scaffolding may be coated with an agent. The agent may be an anti-encrustation agent. An agent may also be disposed within at least one reservoir formed in the scaffolding.

This disclosure also includes an introducer, having an elongated tubular member with a holder at a distal end. The holder may releasably secures a scaffolding with opposing tissue-engaging portions and at least one expansion member in a compressed configuration. A pushing element may be slidably disposed within a lumen of the elongated tubular member, such that relative distal movement of the pushing element detaches the scaffolding from the holder.

In one aspect, the holder may have opposing wings that releasably attach to the tissue-engaging portions of the scaffold.

In one aspect, the holder may be secured at the distal end of the elongated tubular member and may be configured to rotate between being longitudinally aligned with the elongated tubular member and being perpendicular to the elongated tubular member. Control lines may be secured to opposing ends of the holder.

This disclosure also includes a method for increasing a cross-sectional area of a body lumen. The method may involve providing an introducer with an elongated tubular member having a holder at a distal end and a scaffolding releasably secured by the holder in a compressed configuration, wherein the scaffolding has opposing tissue-engaging portions and at least one expansion member. The elongated tubular member may be advanced through a patient until the scaffolding is at a desired position within the body lumen.

The scaffolding may be detached from the holder so that the scaffolding exhibits a deployed configuration, with an increased distance between the tissue-engaging portions as compared to the compressed configuration.

In one aspect, detaching the scaffolding from the holder may involve moving a pushing element slidably disposed within a lumen of the elongated tubular member distally.

In one aspect, the scaffolding may have a pair of expansion members coupled by a pivot, such that the method also involves providing a tether secured to the pivot and removing the scaffolding from the deployed configuration within the body lumen by applying sufficient tension to the tether to cause the expansion members to deflect with respect to each other.

In one aspect, the holder may be rotatably secured to the distal end of the elongated tubular member, such that the elongated tubular member may be advanced though the patient with the holder longitudinally aligned with the elongated tubular member. The method may further involve rotating the holder to a perpendicular configuration before detaching the scaffolding.

In one aspect, the scaffolding may be detached from the holder within a prostatic urethra, such that the deployed configuration of the scaffolding displaces obstructing prostatic lobe tissue.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIG. 5 depicts a schematic view of a scaffolding having uni-directional expansion members in a compressed configuration, with tissue-engaging portions secured to shafts of the expansion member, according to one embodiment.

FIG. 6 depicts a schematic view of a scaffolding having uni-directional expansion members in a deployed configuration, with tissue-engaging portions secured to shafts of the expansion member, according to one embodiment.

FIG. 7 depicts a schematic view of a scaffolding having uni-directional expansion members in a deflected configuration, with tissue-engaging portions secured to shafts of the expansion member, according to one embodiment.

FIG. 8 depicts a schematic view of a scaffolding having uni-directional expansion members in a deflected configuration, with tissue-engaging portions secured to shafts of the expansion member, deployed to expand obstructing prostatic lobe tissues, according to one embodiment.

DETAILED DESCRIPTION

Figure 1:
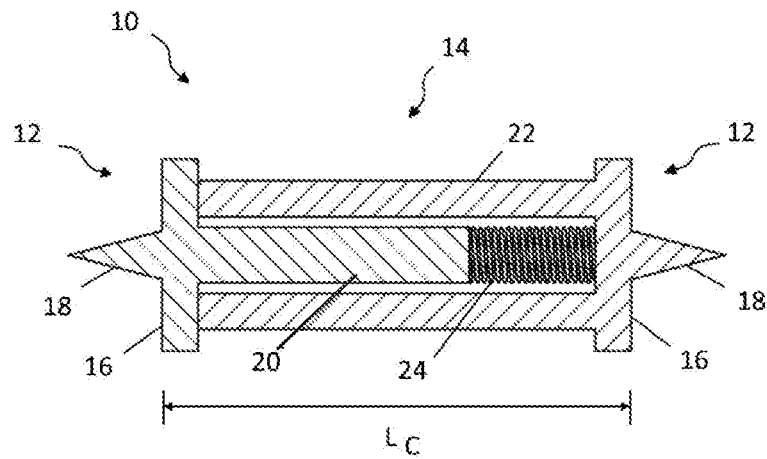
FIG. 1 depicts a schematic view of a scaffolding having a bi-directional expansion member in a compressed configuration, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. Moreover, as used in this specification and the appended claims, the singular forms "a, "an" and "the" include plural referents unless the content clearly dictates otherwise.

As noted above, it would be desirable to provide devices and methods for managing BPH or for performing other procedures associated with increasing or maintaining patency of a body lumen. To that end, a scaffolding may be provided having tissue-engaging portions disposed at opposing ends of an expansion member. The expansion member may have a compressed configuration exhibiting a reduced distance between the tissue-engaging portions and may have a deployed configuration exhibiting an increased distance between the tissue-engaging portions. The scaffolding may be positioned within a body lumen with the expansion member in its compressed configuration. Thereafter, the expansion member may assume a deployed configuration, in which the tissue-engaging portions exert force against the surfaces of the body lumen, displacing tissue laterally. Accordingly, the scaffolding when in the deployed configuration may urge the tissue bordering the body lumen apart to maintain or increase patency. For example, the tissue may be the prostrate and the lumen may be the urethra, such that the scaffolding facilitates management of BPH.

Figure 2:
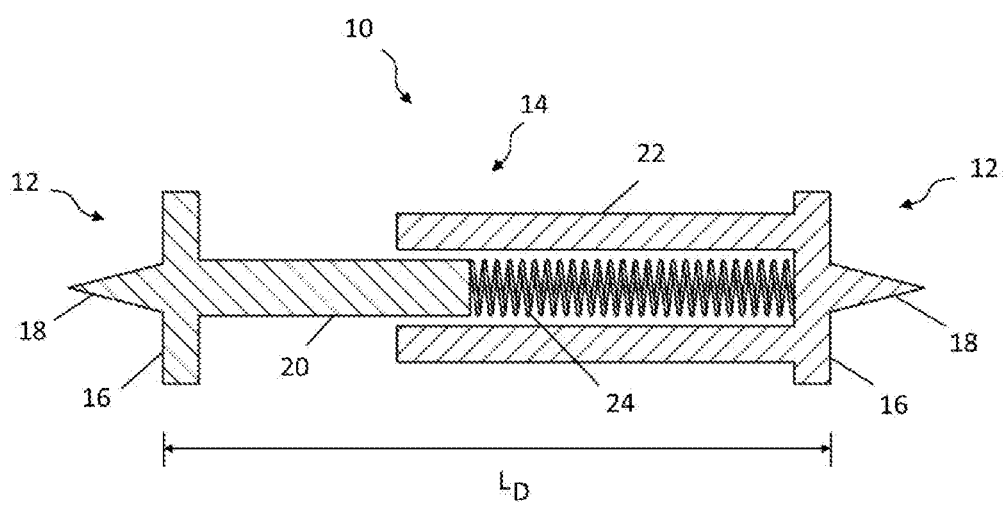
FIG. 2 depicts a schematic view of a scaffolding having a bi-directional expansion member in a deployed configuration, according to one embodiment.

To help illustrate as aspects of this disclosure, FIGS. 1 and 2 schematically depict one embodiment of scaffolding 10, with tissue-engaging portions 12 positioned at opposing ends of expansion member 14. As shown, each tissue-engaging portion 12 may have a lateral plate 16 and tissue anchor 18. Lateral plate 16 may present an increased surface area relative to the nominal diameter of expansion member 14 to facilitate tissue engagement, but are optional and may be omitted in other embodiments. Tissue anchor 18 may have a configuration, such as a prong or other sharpened shape, to releasably secure tissue and reduce the chance of scaffolding 10 being unintentionally disengaged, but is also optional. In this embodiment, expansion member 14 may be bidirectional, with either end forming tissue-engaging portions 12. As shown, expansion member 14 may feature a telescoping arrangement between shaft 20, which carries one tissue-engaging portion 12 and housing 22, which carries the other tissue-engaging portion 12. As used herein, the term "telescoping" means that at least a portion the shaft is configured to extend coaxially within at least a portion of the housing. The profiles of shaft 20 and housing 22 may be circular, oval, square, rectangular or any other suitable shape. In other embodiments, expansion member 14 may be formed from any suitable longitudinally-extending mechanism. A driving element 24, such as a spring or other functionally similar structure, is positioned coaxially within housing 22 and may bias shaft 20 outwards. Scaffolding 10 is shown in FIG. 1 in the compressed configuration, such that the distance $L_C$ corresponds to a reduced distance between tissue-engaging portions 12. Correspondingly, FIG. 2 depicts scaffolding 10 in a deployed configuration, characterized by the distance $L_D$ between tissue-engaging portions 12 being increased relative to $L_C$. As will be appreciated, the distance $L_D$ may vary, depending on the amount of resistance offered by the tissues being displaced.

Figure 3:
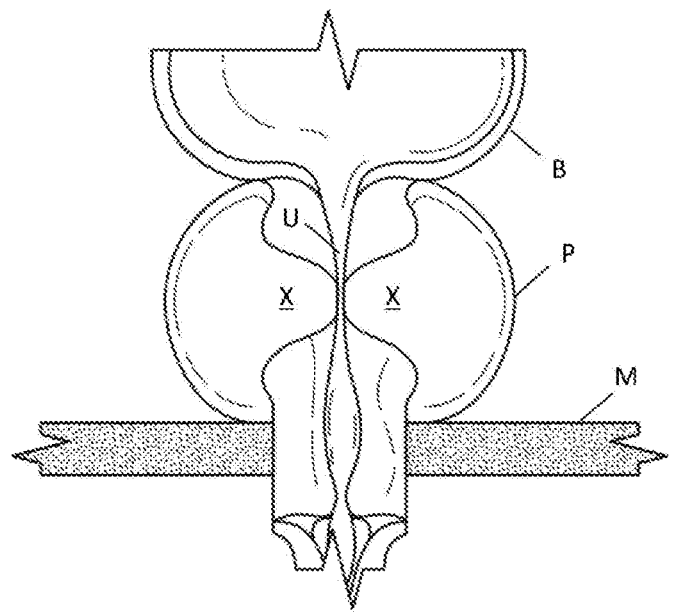
FIG. 3 depicts a schematic view of a prostatic urethra and surrounding anatomy.
Figure 4:
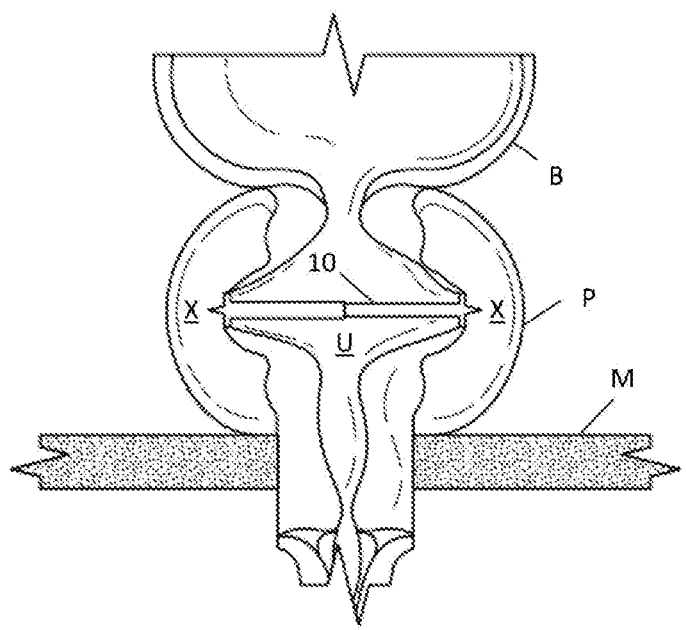
FIG. 4 depicts a schematic view of a scaffolding having a bi-directional expansion member deployed to expand obstructing prostatic lobe tissues, according to one embodiment.

In one exemplary application, scaffolding 10 may be used to manage BPH by increasing the lumen diameter or cross-sectional area of the prostatic urethra. For example, FIG. 3 schematically depicts relevant portions of a patient's anatomy, including the bladder (B), prostate (P), prostatic urethra (U), obstructing prostatic lobe tissues (X), and pelvic floor muscle and external urinary sphincter (M). Although not shown schematically shown in this diagram, the prostatic urethra (U) may become partially compressed by the obstructing prostatic lobe tissues (X). Correspondingly, FIG. 4 schematically depicts scaffolding 10 in a deployed configuration within the prostatic urethra (U). As may be seen, scaffolding 10 is deployed within the prostatic urethra (U) such that the prostatic urethra (U) and the obstructing prostatic lobe tissues (X) are displaced or otherwise pushed laterally apart by scaffolding 10 in its deployed configuration to increase the cross-sectional area of the prostatic urethra (U).

Another embodiment of this disclosure is schematically depicted in FIGS. 5-7, with respect to scaffolding 30 which also has tissue-engaging portions 32 positioned at opposing ends of a pair of uni-directional expansion members 34. As described above, each tissue-engaging portion 32 may have a lateral plate 36 and tissue anchor 38, in a similar manner as described above. Each uni-directional expansion member 34 may comprise a telescoping arrangement between shaft 40, which carries one tissue-engaging portion 32 each, and housing 42. As in other embodiments, the profiles of each expansion member 34 may be any desirable shape, and may employ any suitable expandable mechanism as known to those of skill in the art having an elongation capability comparable to the telescoping embodiments. Generally, the expansion members may be considered to exhibit longitudinal rather than radial extension. Driving elements 44 are positioned coaxially within each housing 42 and configured to bias shaft 40 outwards. Uni-directional expansion members 34 may be coupled by pivot 46 at housings 42, which may be a spring or other similarly resilient member that biases expansion member 34 into a longitudinally aligned configuration, but also allows deflection at the junction to facilitate insertion and/or removal of scaffolding 30 from a body lumen. Scaffolding 30 is shown in FIG. 5 in the compressed configuration, with a reduced distance between tissue-engaging portions 32 similar to that described above, and shown in FIG. 6 in a deployed configuration, again characterized by an increased distance between tissue-engaging portions 32. Further, FIG. 7 schematically depicts deflection between uni-directional expansion members 34, occurring at pivot 46. Although shown in the context of the deflection occurring while expansion member 34 are in a deployed configuration, it will be appreciated that pivot 46 also allows deflection when expansion members 34 are in the compressed configuration, such as shown in FIG. 5.

FIG. 8 schematically depicts scaffolding 30 in a deployed configuration. As shown, the prostatic urethra (U) and obstructing prostatic lobe tissues (X) are displaced or otherwise pushed laterally apart by scaffolding 30 in its deployed configuration to increase the cross-sectional area of the prostatic urethra (U).

Figure 9:
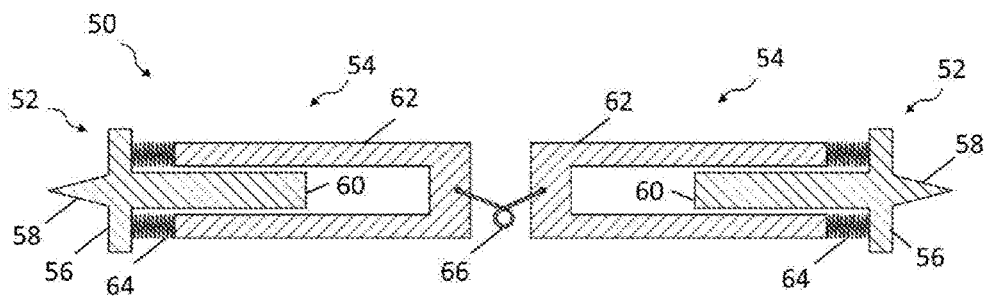
FIG. 9 depicts a schematic view of a scaffolding having uni-directional expansion members in a compressed configuration, with tissue-engaging portions secured to shafts of the expansion member, according to another embodiment.
Figure 10:
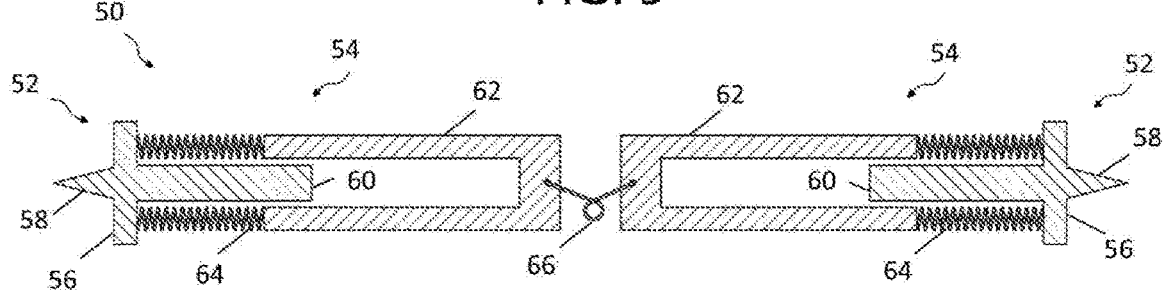
FIG. 10 depicts a schematic view of a scaffolding having uni-directional expansion members in a deployed configuration, with tissue-engaging portions secured to shafts of the expansion member, according to another embodiment.
Figure 11:
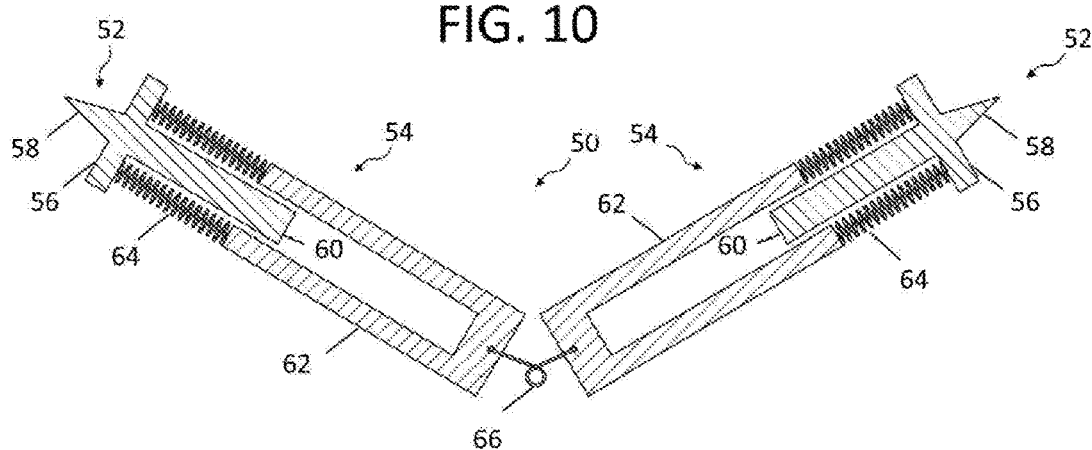
FIG. 11 depicts a schematic view of a scaffolding having uni-directional expansion members in a deflected configuration, with tissue-engaging portions secured to shafts of the expansion member, according to another embodiment.

A related embodiment is schematically depicted in FIGS. 9-11, in which scaffolding 50 also has tissue-engaging portions 52 and a pair of uni-directional expansion members 54, each with lateral plates 56 and tissue anchors 58 as described above. Also similarly, the telescoping arrangement of uni-directional expansion members 54 is formed by shaft 60, each of which carries one tissue-engaging portion 52, and housing 62. However, in this alternate embodiment, each expansion member 54 has one or more driving elements 64 positioned longitudinally adjacent shaft 60 and configured to bias it outwards. Notably, one or more driving elements 64 may be positioned at points around the perimeter of shaft 60 or a single driving element 64 may be coaxially disposed around shaft 60. Again, uni-directional expansion members 54 may be coupled by pivot 66 at housings 62 as described above. Scaffolding 50 is shown in FIG. 9 in the compressed configuration, with a reduced distance between tissue-engaging portions 52 similar to that described above, and shown in FIG. 10 in a deployed configuration, also characterized by an increased distance between tissue-engaging portions 52. Still further, FIG. 11 schematically depicts deflection between uni-directional expansion members 54, occurring at pivot 66. Scaffolding 50 may be employed in a similar manner to scaffolding 30 as shown in FIG. 8.

Figure 12:
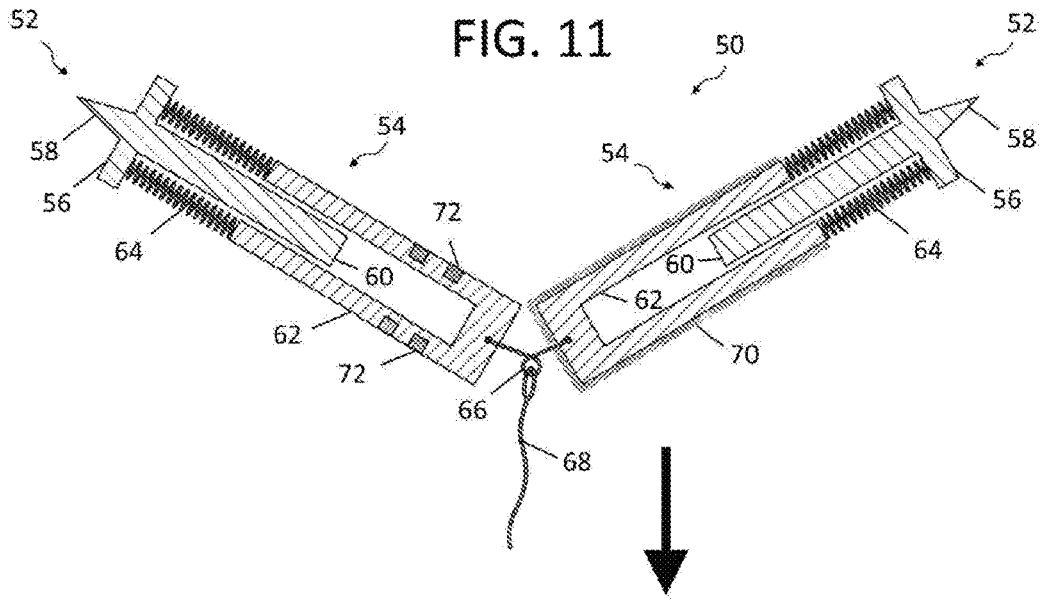
FIG. 12 depicts a schematic view of a scaffolding having uni-directional expansion members in a deflected configuration, with a tether secured to a pivot coupling the expansion members, according to another embodiment.

Further, FIG. 12 schematically depicts scaffolding 50 with tether 68 attached to pivot 66. As will be appreciated, tension applied to tether 68 in the indicated direction may help cause expansion member 54 to deflect at pivot 66, to further facilitate placement and/or removal of scaffolding 50 within a patient's lumen. Additionally, FIG. 12 also shows scaffolding 50 having an optional coating 70. In this embodiment, coating 70 is applied to the outside of housing 62, but may be applied to any surface portion of scaffolding 50 and may cover any desired amount of the scaffolding 50, including substantially the entire exterior surface. Coating 70 may be one or more therapeutic agents alone or may be one or more agents retained in a polymeric matrix configured to release the agent(s) in a controlled manner. Coating 70 may include an agent that prevents or reduces encrustation in a urinary environment. An agent may also be provided that prevents or reduces endotheliazation or other tissue ingrowth. Still further, the agent may be used for any suitable therapeutic purpose. Alternatively or in addition, one or more agent(s), alone or in a polymeric matrix, may be deposited in reservoirs 72. Any desired number of reservoirs 72, such as one or more, may be employed as warranted depending on factors such as the amount of agent to be delivered.

Figure 13:
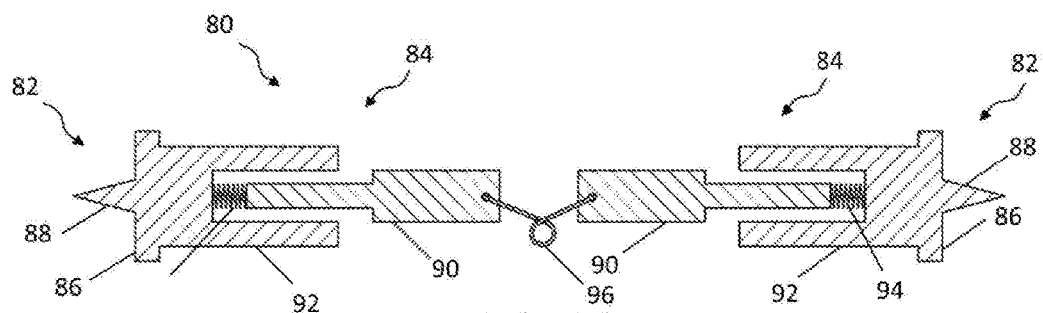
FIG. 13 depicts a schematic view of a scaffolding having uni-directional expansion members in a compressed configuration, with tissue-engaging portions secured to housings of the expansion member, according to one embodiment.
Figure 14:
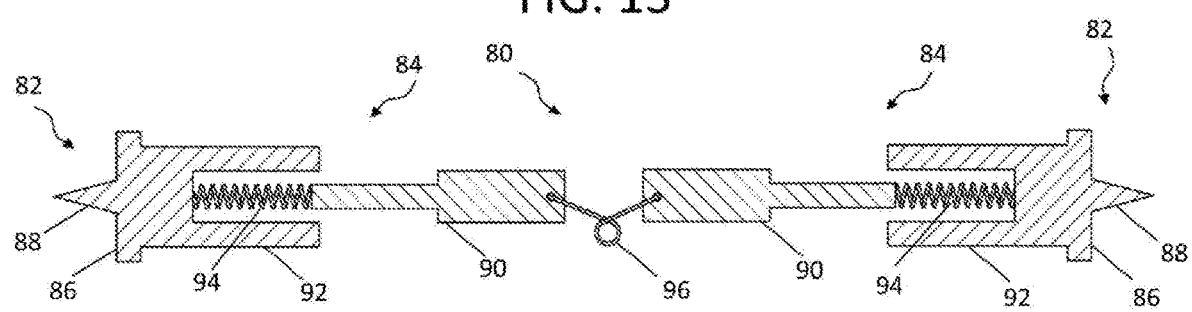
FIG. 14 depicts a schematic view of a scaffolding having uni-directional expansion members in a deployed configuration, with tissue-engaging portions secured to housings of the expansion member, according to one embodiment.
Figure 15:
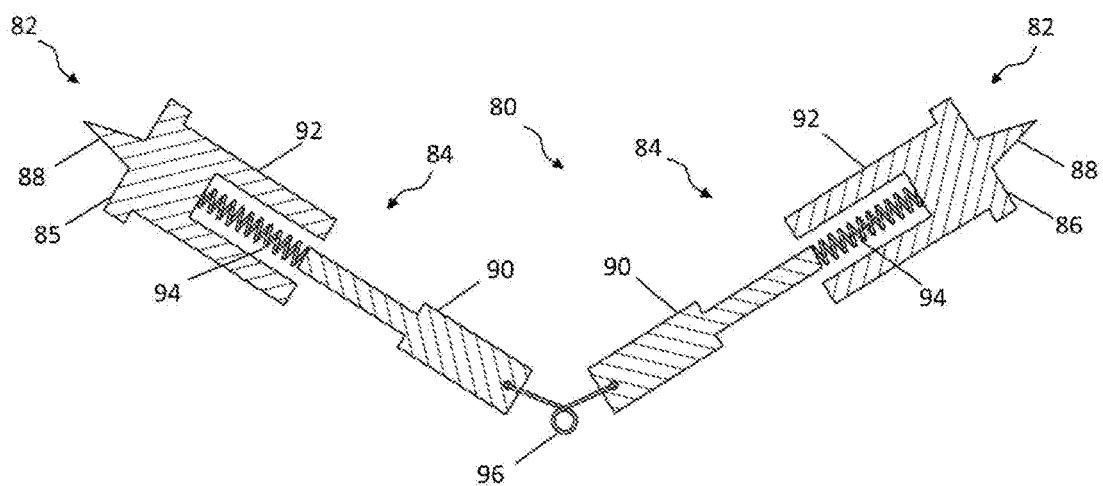
FIG. 15 depicts a schematic view of a scaffolding having uni-directional expansion members in a deflected configuration, with tissue-engaging portions secured to housings of the expansion member, according to one embodiment.

Yet another embodiment of this disclosure is schematically depicted in FIGS. 13-15, with respect to scaffolding 80 which also has tissue-engaging portions 82 positioned at opposing ends of a pair of uni-directional expansion members 84. As described above, each tissue-engaging portion 82 may have a lateral plate 86 and tissue anchor 88, again as described above. Each uni-directional expansion member 84 may comprise a telescoping arrangement between shaft 90 and housing 92. In this embodiment, each tissue-engaging portion 82 is disposed at the end of each housing 92. Once more, the profiles of each expansion member 84 may be any desirable shape, and may employ any suitable expandable mechanism having an elongation capability comparable to the telescoping embodiments as known to those of skill in the art. Driving elements 94 are positioned coaxially within each housing 92 and configured to bias housing 92 outwards. Uni-directional expansion members 84 may be coupled at shafts 90 by pivot 96, which may be a spring or other similarly resilient member that biases expansion member 84 into a longitudinally aligned configuration, but also allows deflection at the junction to facilitate insertion and/or removal of scaffolding 80 from a body lumen. Scaffolding 80 is shown in FIG. 13 in the compressed configuration, with a reduced distance between tissue-engaging portions 82 similar to that described above, and shown in FIG. 14 in a deployed configuration, again characterized by an increased distance between tissue-engaging portions 82. Similarly, FIG. 15 schematically depicts deflection between uni-directional expansion members 84, occurring at pivot 96. Scaffolding 80 may be employed in a similar manner to scaffolding 30 as shown in FIG. 8.

Figure 16:
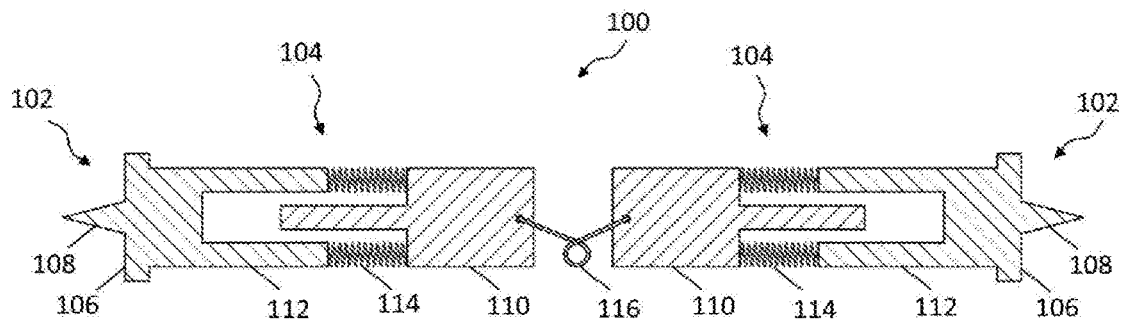
FIG. 16 depicts a schematic view of a scaffolding having uni-directional expansion members in a compressed configuration, with tissue-engaging portions secured to housings of the expansion member, according to another embodiment.
Figure 17:
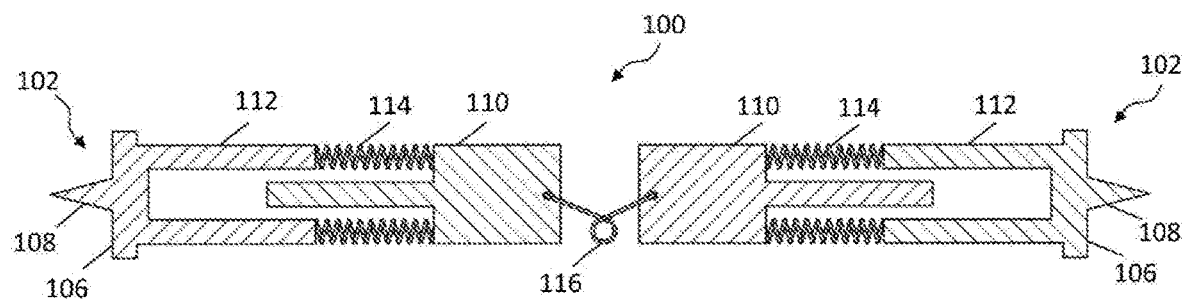
FIG. 17 depicts a schematic view of a scaffolding having uni-directional expansion members in a deployed configuration, with tissue-engaging portions secured to housings of the expansion member, according to another embodiment.
Figure 18:
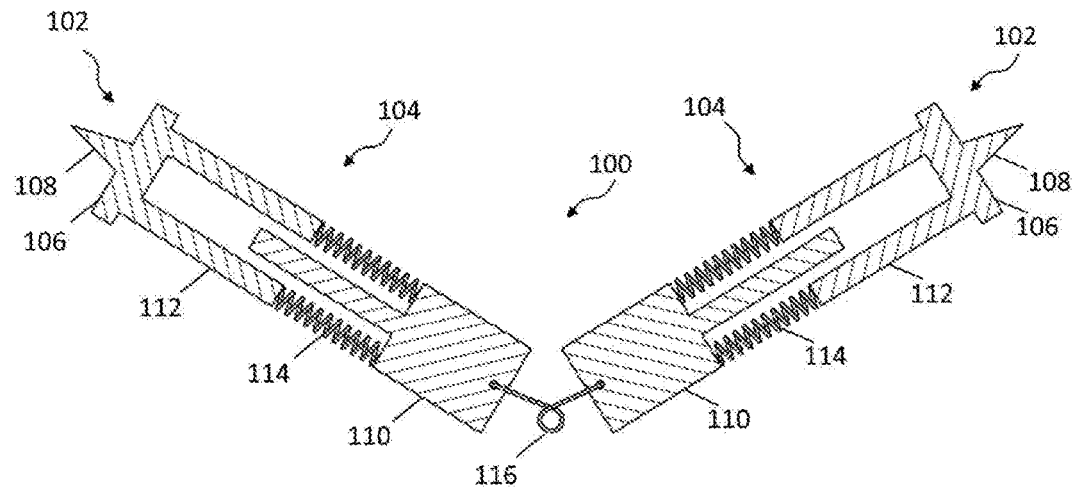
FIG. 18 depicts a schematic view of a scaffolding having uni-directional housings members in a deflected configuration, with tissue-engaging portions secured to shafts of the expansion member, according to another embodiment.

Another related embodiment is schematically depicted in FIGS. 16-18, in which scaffolding 100 also has tissue-engaging portions 102 and a pair of uni-directional expansion members 104, each with lateral plates 106 and tissue anchors 108 as described above. Also similarly, the telescoping arrangement of uni-directional expansion members 104 is formed with shaft 110 and housing 112, each of which carries one tissue-engaging portion 102. In this alternate embodiment, each expansion member 104 has one or more driving elements 114 positioned longitudinally adjacent shaft 110 and configured to bias housing 112 outwards. Notably, one or more driving elements 114 may be positioned at points around the perimeter of shaft 110 or a single driving element 114 may be coaxially disposed around shaft 110. Again, uni-directional expansion members 104 may be coupled by pivot 116 at shafts 110. Scaffolding 100 is shown in FIG. 16 in the compressed configuration, with a reduced distance between tissue-engaging portions 102 similar to that described above, and shown in FIG. 17 in a deployed configuration, also characterized by an increased distance between tissue-engaging portions 102. Still further, FIG. 18 schematically depicts deflection between uni-directional expansion members 104, occurring at pivot 116. Scaffolding 100 may be employed in a similar manner as shown with regard to scaffolding 30 in FIG. 8.

Figure 19:
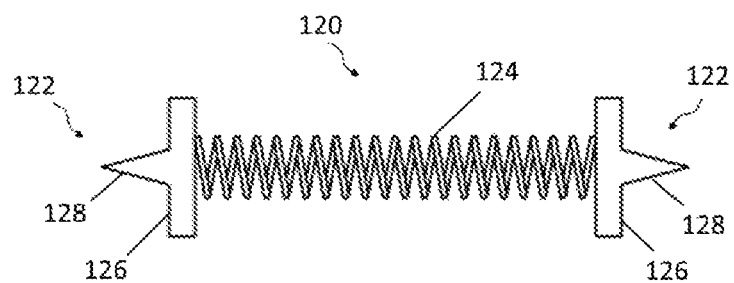
FIG. 19 depicts a schematic view of a scaffolding having a bi-directional non-telescoping expansion member in a compressed configuration, according to one embodiment.
Figure 20:
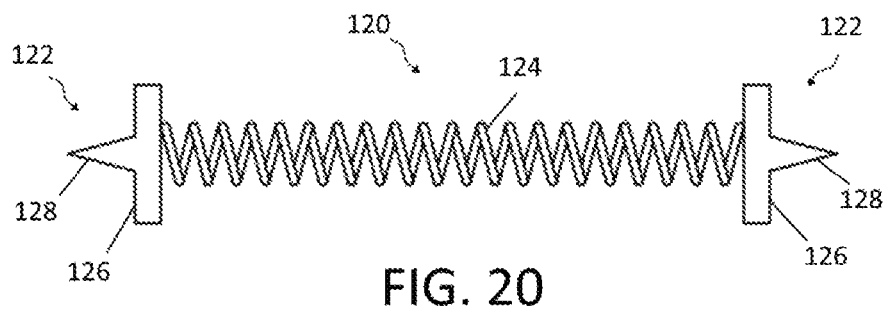
FIG. 20 depicts a schematic view of a scaffolding having a bi-directional non-telescoping expansion member in a deployed configuration, according to one embodiment.
Figure 21:
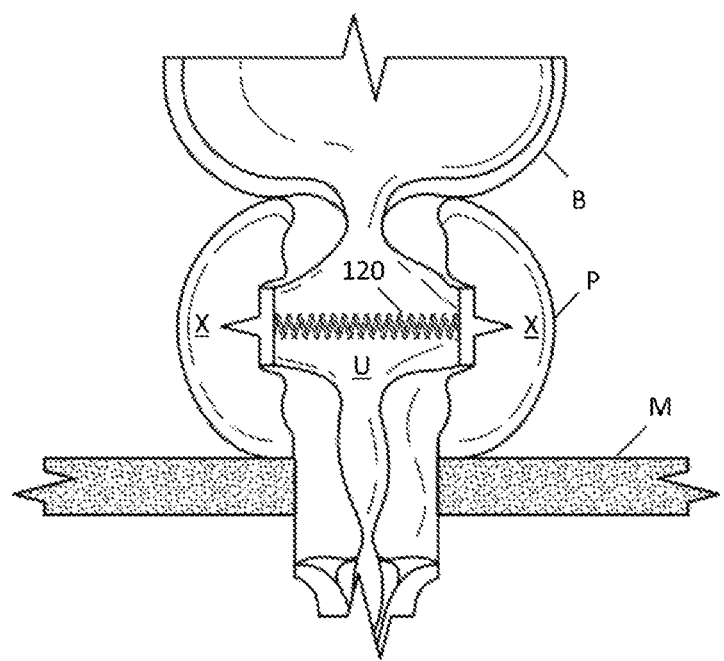
FIG. 21 depicts a schematic view of a scaffolding having a bi-directional non-telescoping expansion member deployed in a prostatic urethra, according to one embodiment.

Another embodiment of this disclosure is schematically depicted in FIGS. 19 and 20. As shown, scaffolding 120 has tissue-engaging portions 122 positioned at opposing ends of bi-directional expansion member 124. In line with the discussion above, each tissue-engaging portion 122 may have a lateral plate 126 and tissue anchor 128. In this embodiment, expansion member 124 may be a longitudinally-extendable structure, configured as a spring. Scaffolding 120 is shown in FIG. 19 in the compressed configuration, with a reduced distance between tissue-engaging portions 122, and expansion member 124 may be biased towards a deployed configuration as shown in FIG. 20, with an increased distance between tissue-engaging portions 122. Scaffolding 120 may be used to manage BPH similar to the other embodiments described above, by increasing the lumen diameter or cross-sectional area of the prostatic urethra. Although not shown for illustration purposes, as schematically depicted in FIG. 21, when scaffolding 120 is positioned within the prostatic urethra (U) in a deployed configuration, the obstructing prostatic lobe tissues (X) may be displaced or otherwise pushed laterally apart. Thus, when scaffolding 120 is in its deployed configuration, it may increase the cross-sectional area of the prostatic urethra (U).

Figure 22:
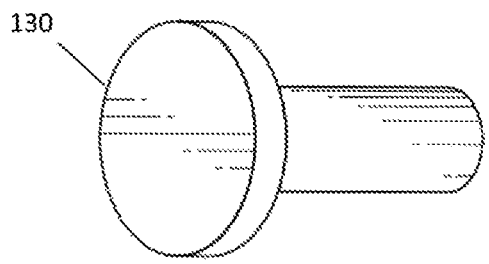
FIGS. 22-25 depict schematic views of a different configurations of lateral plates and anchors of tissue-engaging portions of a scaffolding, according to various embodiment.
Figure 23:
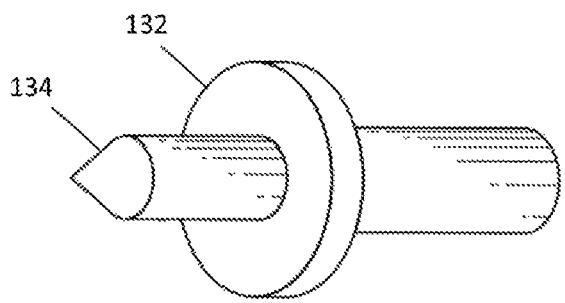
Figure 24:
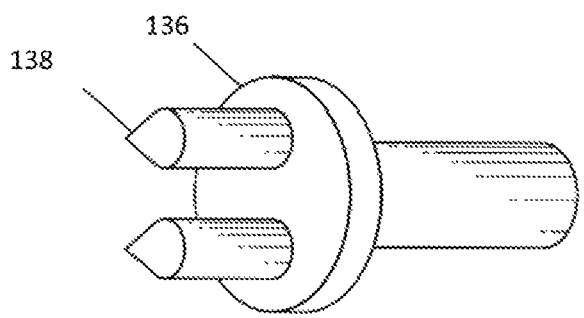
Figure 25:
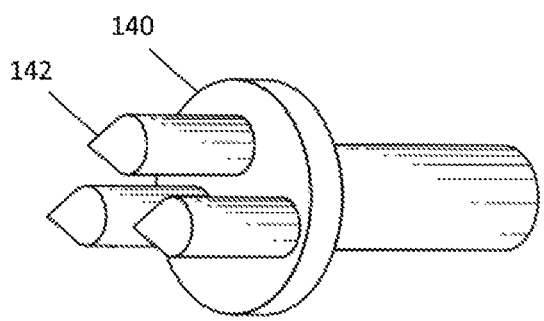

As discussed above, the various tissue-engaging portions of the scaffoldings of this disclosure may optionally feature lateral plates and/or anchors in some embodiments. Various exemplary configurations are shown in FIGS. 22-25, with FIG. 22 schematically showing a tissue-engaging portion having lateral plate 130 and no anchor, FIG. 23 schematically showing a tissue-engaging portion having lateral plate 132 and an anchor formed by a single prong 134, FIG. 24 schematically showing a tissue-engaging portion having lateral plate 136 and an anchor formed by a pair of prongs 138, and FIG. 25 schematically showing a tissue-engaging portion having lateral plate 140 and an anchor formed by three prongs 142. The anchor may be any suitable configuration designed to enhance friction and further secure the contact between the scaffold device and the target body tissues obstructing the body lumen (such as prostatic lobe tissues obstructing the urethra), to help reduce disengagement of the scaffold device. The prongs in these embodiments may be elongated, with a sharp-edged form such as a needle and/or spike that allows penetration into the target body tissues. Any other design, configuration and/or dimension may be employed in other embodiments of the disclosure.

Figure 26:
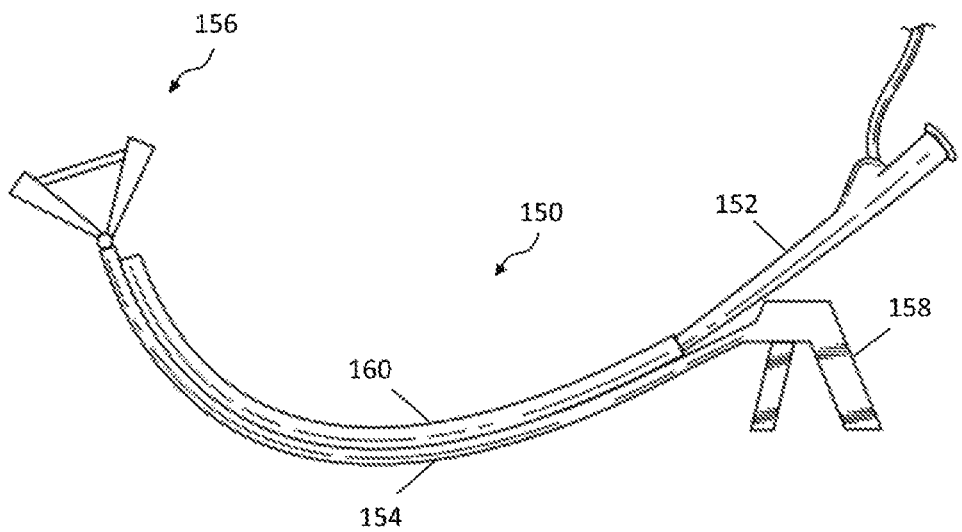
FIG. 26 depicts a schematic view of a scaffolding introducer for use with a flexible endoscope, according to one embodiment.
Figure 27:
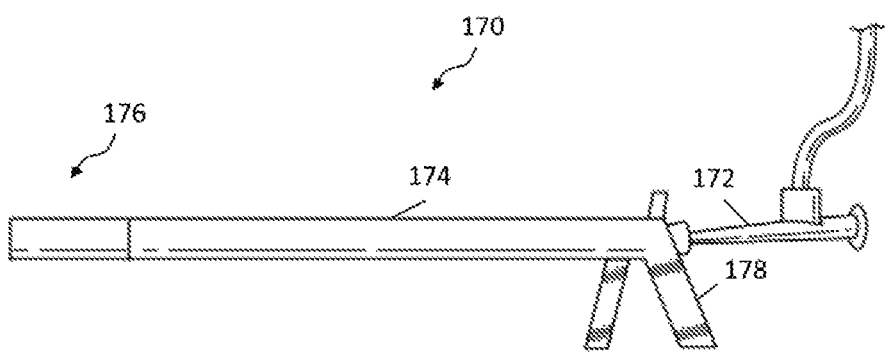
FIG. 27 depicts a schematic view of a scaffolding introducer for use with a rigid endoscope, according to one embodiment.

Delivery of a scaffolding having tissue-engaging portions at opposing ends of one or more expansion members may be accomplished using any suitable introducer or applicator. For example, FIG. 26 schematically depicts an introducer 150 configured for use with a flexible endoscope 152. Introducer 150 may have a flexible, elongated tubular member 154 with a scaffolding releasably secured to distal end 156. Introducer 150 may have an actuator 158 at the proximal end that is configured to allow appropriate placement and release of the scaffolding at a desired location within a body lumen, such as the prostatic urethra when the scaffolding is used for managing BPH. Introducer 150 also features a tubular guide 160 that is longitudinally aligned with at least a portion of elongated member 154, having a lumen (not shown in this view) to receive endoscope 152. As described in more detail below, distal end 156 is in a configuration that facilitates release of the scaffolding within a bodily lumen, including the prostatic urethra for example. Another embodiment is illustrated in FIG. 27 with respect to introducer 170 that is 170 configured for use with a rigid endoscope 172. As above, introducer 170 may have an elongated tubular member 174 with a scaffolding releasably secured to distal end 176 and an actuator 178 at the proximal end that is configured to allow appropriate placement and release of the scaffolding at a desired location within a body lumen. Similarly, a bore (not shown in this view) within tubular member 174 may receive endoscope 172. In other embodiments, either introducer design may be configured to be disposed within a working channel of the endoscope. In this example, distal end 176 is in a configuration with a reduced profile that facilitates advancement through a body lumen. By aligning the introducer with the endoscope as described in the above embodiments, the operator may more readily visualize the distal end of the introducer to facilitate placement of the scaffolding as desired within a body lumen.

Figure 28:
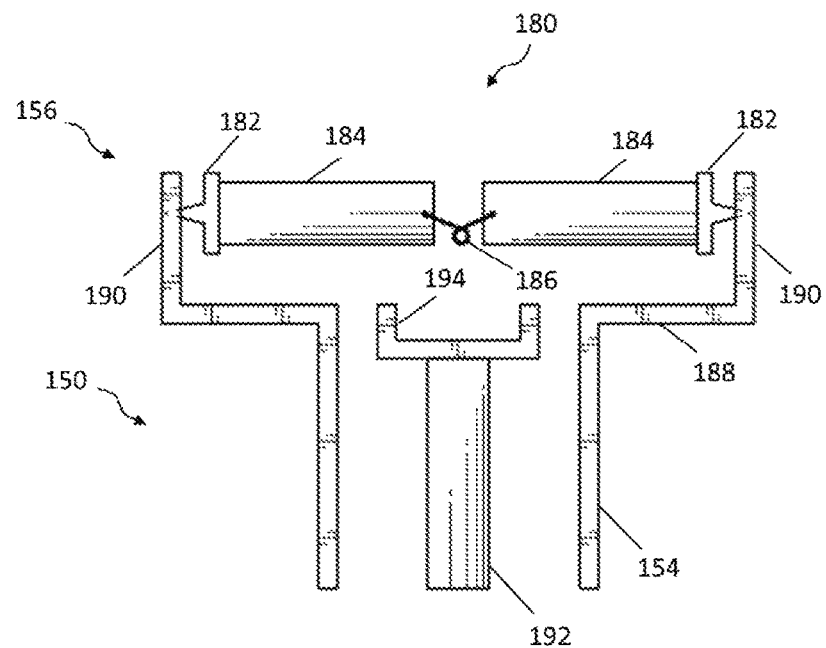
FIG. 28 depicts a schematic view of a distal end of an introducer with a releasably secured scaffolding, according to one embodiment.

Other aspects of this disclosure may be appreciated in the context of the schematic detail views of distal end 154 of introducer 150 shown in FIGS. 28-31. Although discussed in relation to this embodiment, the techniques may be applied to introducer 170 or any other suitable introducer or applicator. As shown in FIG. 28, scaffolding 180, having tissue-engaging portions 182 at opposing ends to a pair of unidirectional expansion members 184 connected by pivot 186, may be releasably secured by holder 188 of distal end 154. In this embodiment, holder 188 features opposing wings 190 that receive tissue-engaging portions 182 of scaffolding 180. Any suitable configuration may be used in other embodiments. Scaffolding 180 may be releasably secured in any desired manner. For example, the outward force associated with the biases of expansion members 184 may cause sufficient friction between tissue-engaging portions 182 and wings 190 to retain scaffolding 180 until positioned at a desired area within a body lumen. Pushing element 192 has a distal end with a pair of projections 194 configured to engage each expansion member 184 and reduce unwanted deflection at pivot 186 during placement of scaffolding 180.

Figure 29:
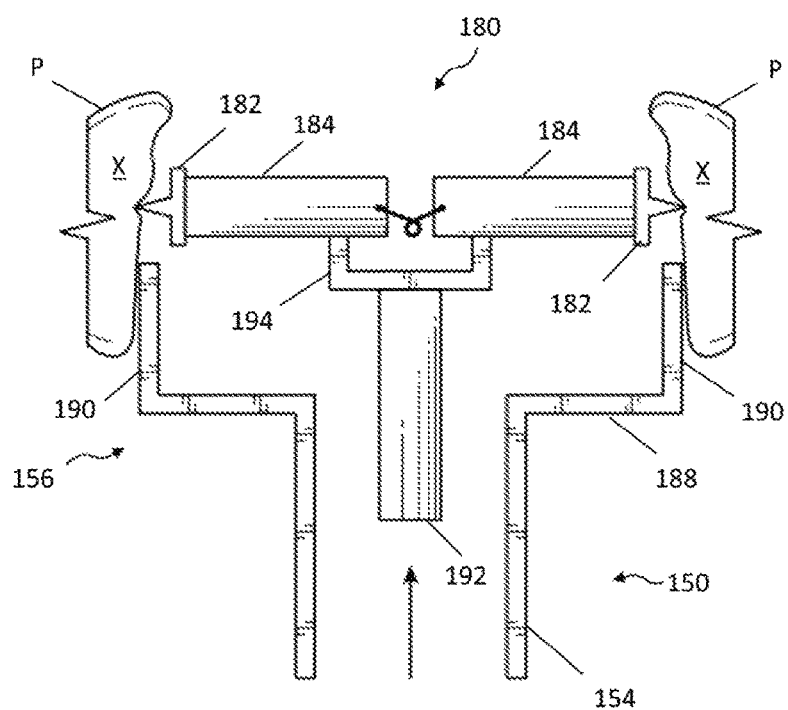
FIG. 29 depicts a schematic view of a distal end of an introducer, with a pushing element detaching a scaffolding, according to one embodiment.
Figure 30:
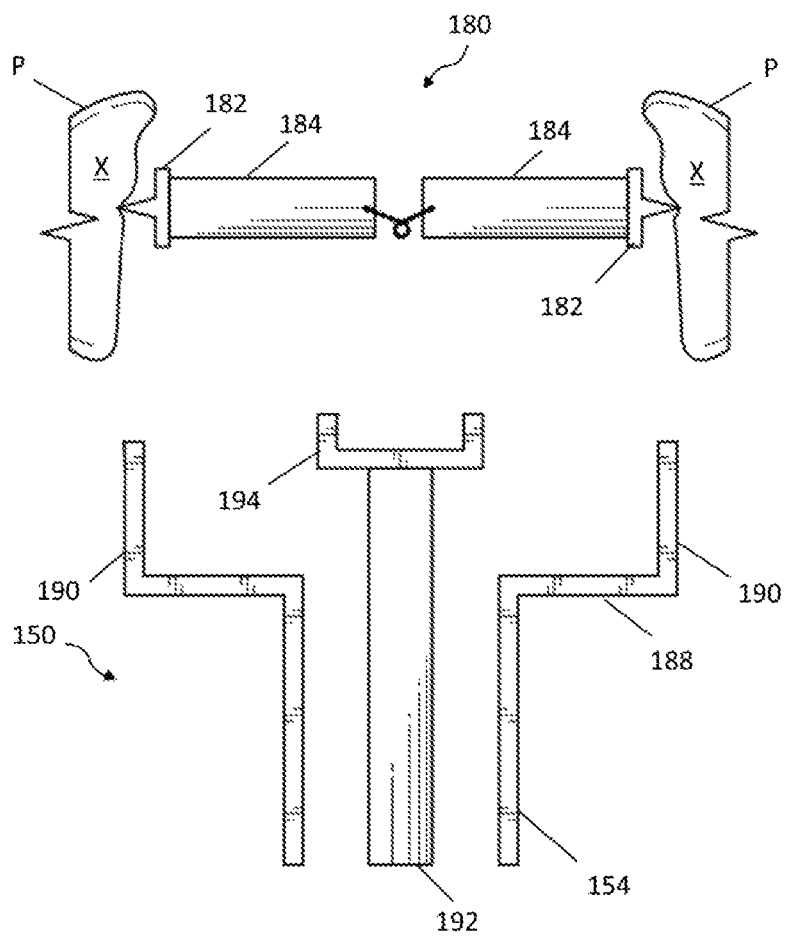
FIG. 30 depicts a schematic view of a distal end of an introducer being withdrawn from a deployed scaffolding, according to one embodiment.
Figure 31:
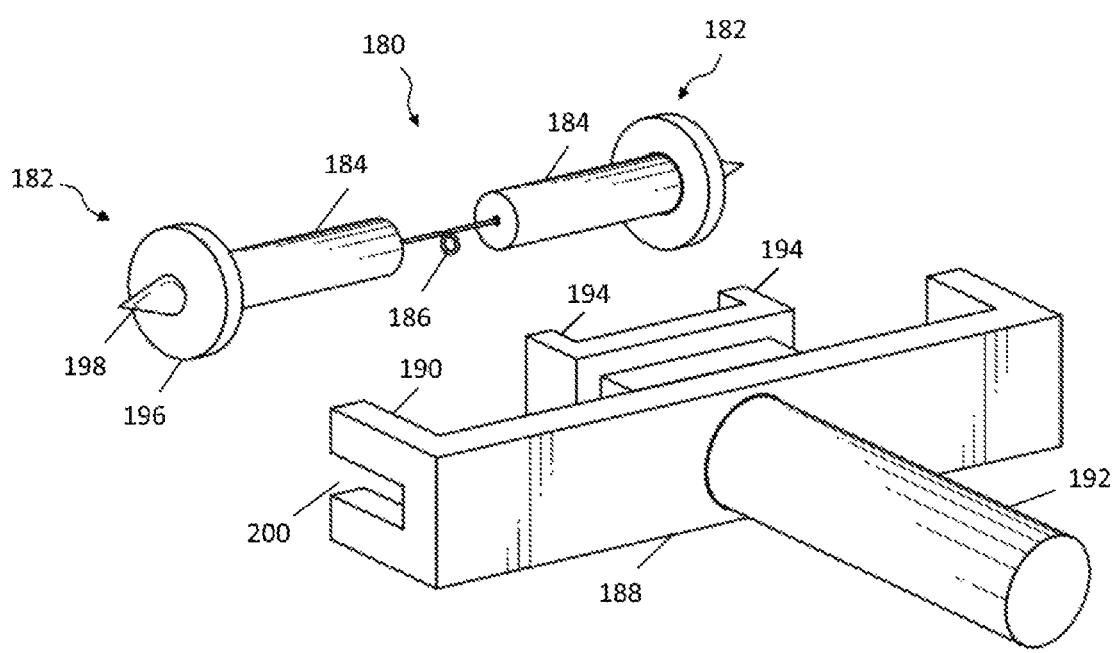
FIG. 31 depicts a partial elevational view of a holder and a detached, deployed scaffolding, according to one embodiment.
Figure 32:
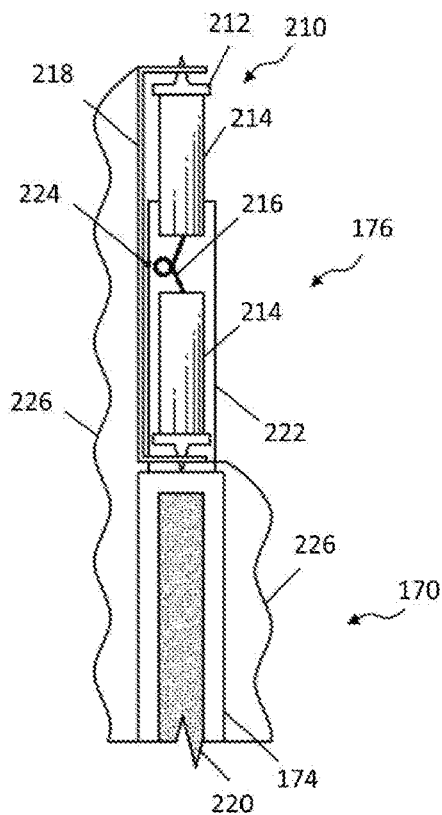
FIG. 32 depicts a schematic view of a distal end of an introducer with a holder in a reduced profile configuration, according to one embodiment.

Further, pushing element 192 may be slidably disposed within a lumen of introducer 150 so that relative distal movement drives scaffolding 180 free from holder as schematically indicated by FIGS. 29-31. For example, FIG. 29 shows distal end 156 having been advanced to a position in which scaffolding 180 is positioned within the prostatic urethra, such that tissue-engaging portions 182 are adjacent portions of obstructing prostatic lobe tissue (X) of prostate (P). Distal movement of pushing element 192 detaches tissue-engaging portions 184 from wings 190 of holder 188, such that expansion members 184 may apply outwards force to lobe tissue (X). Following deployment of scaffolding 180, distal end 156 with holder 188 and pushing element 192 may be withdrawn, leaving scaffolding 180 positioned within the body lumen, displacing or otherwise pushing the obstructing prostatic lobe tissues (X) laterally apart to increase the cross-sectional area of the prostatic urethra to help manage BPH, for example. An elevational view of this configuration of scaffolding 180 and distal end 156 with holder 188 and pushing element 192 is schematically depicted in FIG. 31. As shown, scaffolding 180 has been detached from holder 188 by relative distal movement of pushing element 192. This view illustrates that tissue-engaging portions 182 may have lateral plate 196 and anchor 198 as described above. Anchor 198 may be configured to fit within slot 200 of wings 190 to help releasably secure scaffolding 180 prior to deployment.

Another embodiment of this disclosure is depicted in FIGS. 32-37, which show a transition of distal end 176 of introducer 170 from a reduced, delivery profile, such as shown in FIG. 27, to a deployment profile, in which scaffolding 210 may be detached for deployment within a body lumen. The reduced profile shown in FIG. 32 features scaffolding 210, with tissue-engaging portions 212 opposing a pair of expansion members 214 that are coupled at pivot 216. Although discussed in relation to this embodiment, the techniques may be applied to introducer 150 or any other suitable introducer or applicator. Scaffolding 210 is releasably secured to holder 218 in any appropriate manner, including the techniques described above. Introducer 170 may also have pushing element 220 slidably disposed within a lumen of elongated member 174. Holder 218 is rotatably attached to extension 222 at distal end 176 of elongated member 174 by axle 224. Control lines 226 may be attached at either end of holder 218. In the configuration shown in FIG. 32, holder 218 may be generally in longitudinal alignment with elongated member 174. Correspondingly, the overall profile is reduced to facilitate advancement of introducer 170 and scaffolding 210 through a body lumen.

Figure 33:
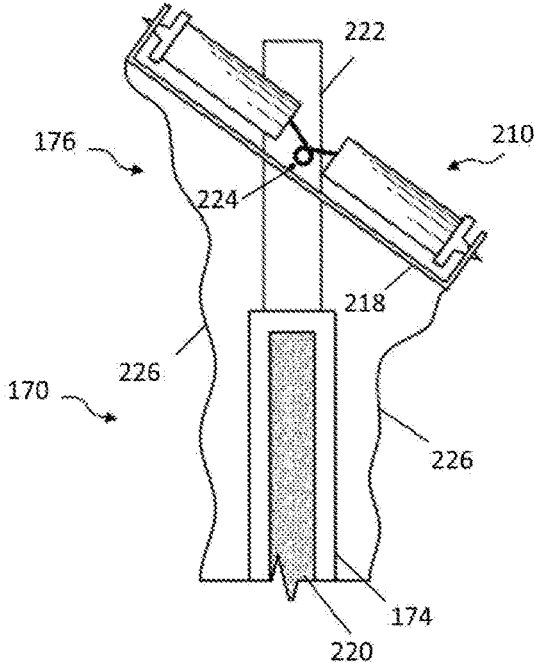
FIG. 33 depicts a schematic view of a distal end of an introducer, with a holder partially rotated into a deployment configuration, according to one embodiment.
Figure 34:
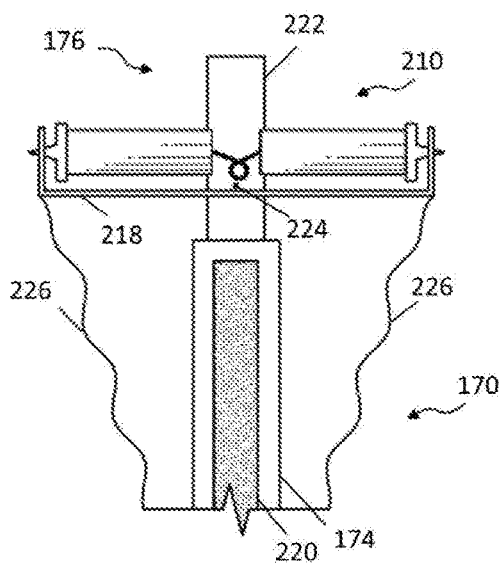
FIG. 34 depicts a schematic view of a distal end of an introducer, with a holder rotated into a deployment configuration, according to one embodiment.
Figure 35:
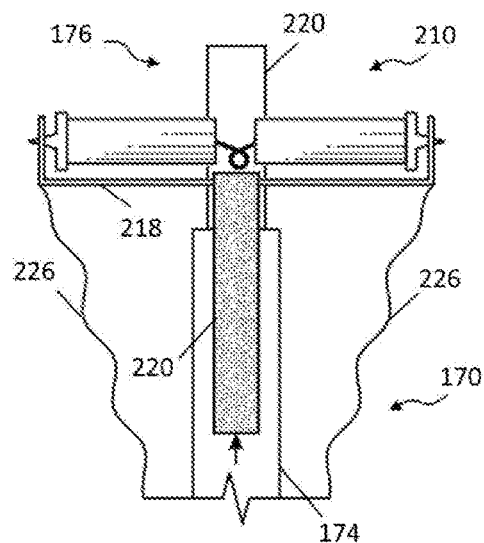
FIG. 35 depicts a schematic view of a distal end of an introducer, with a holder rotated into a deployment configuration and a pushing element being moved distally to detach a scaffolding, according to one embodiment.
Figure 36:
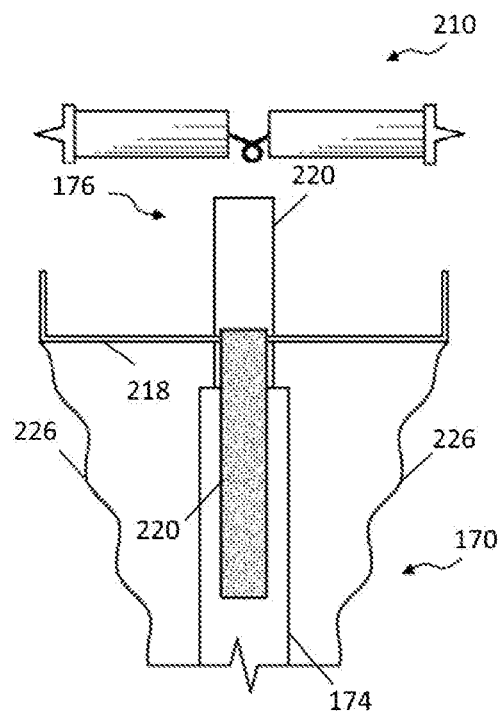
FIG. 36 depicts a schematic view of an introducer with a holder rotated into deployment configuration being withdrawn from a deployed scaffolding, according to one embodiment
Figure 37:
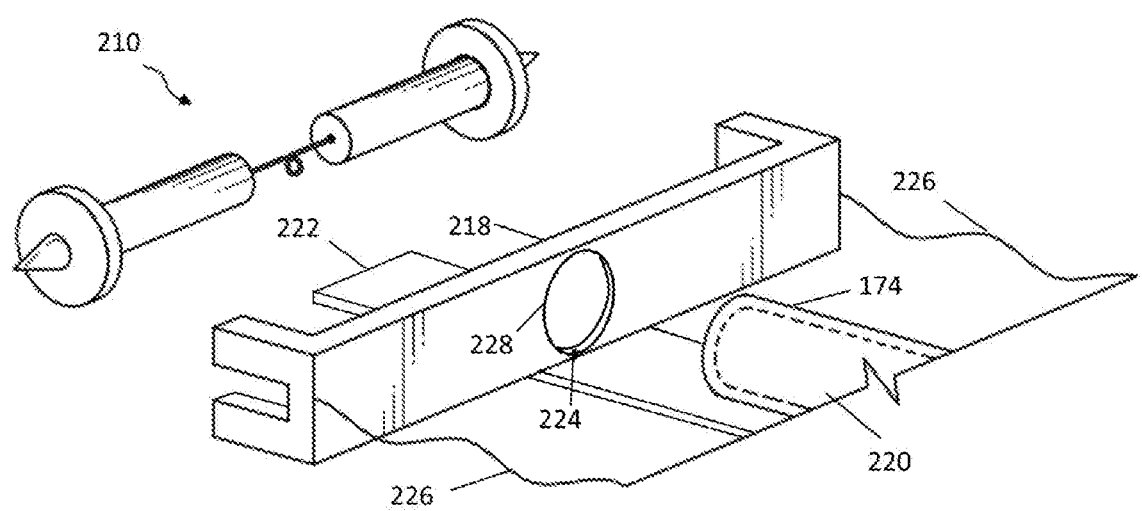
FIG. 37 depicts a partial elevational view of a holder rotated into deployment configuration and a detached, deployed scaffolding, according to one embodiment.

Once scaffolding 210 has been positioned at a desired location within the body lumen, appropriate manipulation of control lines 226 may adjust rotation of holder 218 around axle 224 to impart a deployment configuration. For example, FIG. 33 shows holder 218 after being partially rotated around axle 224 from the reduced profile. Further rotation of holder 218 may result in a configuration in which holder 218 is generally perpendicular to the longitudinal axis of elongated member 174 as shown in FIG. 34. In this configuration, pushing element 220 may be moved distally in the direction of the arrow indicated in FIG. 35 to detach scaffolding 210 from holder 218 in a similar manner to the embodiments described above. Pushing element 220 may extend through an aperture 228 (not shown in this view) in holder 218 to engage and detach scaffolding 210. Notably, FIG. 36 shows deployment of scaffolding 210 and withdrawal of distal end 176 and holder 218. An elevational view of this configuration of scaffolding 210 and distal end 176 is schematically depicted in FIG. 37. As shown, scaffolding 210 has been detached from holder 218 and pushing element 220 (shown in phantom) has been withdrawn proximally, through aperture 228 and within elongated member 174. In alternative embodiments, the rotational attachment of holder 218 to extension 222 at axle 224 may be driven by a spring or similar element, to cause the transition between the reduced profile (with holder 218 longitudinally aligned with elongated member 174) and the deployment profile (with holder 218 generally perpendicular to the longitudinal axis of elongated member 174) automatically, so that control lines 226 are not needed.

The component parts of the scaffoldings and/or introducers of this disclosure may be formed from any suitable material or combination of materials, including polymers and metal alloys. In some embodiments, one or more of the components of the scaffolding may be biodegradable and/or bioabsorbable. As noted above, some or all portions of the scaffolding may be treated or coated with a material configured to reduce encrustation within a urinary environment. The scaffoldings may also be coated with any other therapeutic or otherwise active agent. As desired, the introducers of this disclosure may be reusable or disposable.

From the above discussion, it will be appreciated that the scaffoldings of this disclosure may be employed to increase the cross-sectional area of a body lumen. The scaffoldings may have one or more expansion members, that exhibit longitudinal extension and non-radial expansion. The expansion member(s) transition between a compressed configuration, with a reduced distance between opposing tissue-engaging portions, and a deployed configuration, with an increased distance between opposing tissue-engaging portions. When in the deployed configuration, the scaffolding may increase the cross-sectional area of a body lumen. The scaffolding may be an implant, capable of being securely attached to the body lumen, and may be removable. During removal, one or more of the expansion members may be returned to the compressed configuration. The scaffolding may be deployed in a body lumen in various locations, including the urinary system, such as within the urethra, and used to manage or treat benign prostatic hyperplasia, the cardiovascular system, such as within a blood vessel, the gastrointestinal system, such as within the biliary duct, and the respiratory system, such as within the trachea. The scaffolding may be placed with an introducer as noted above, such as with the guidance of an endoscope. Further, removal of the scaffolding from the body lumen may not require the use of an endoscope. For example, pulling a tether secured to a pivot coupling a pair of expansion members may cause the scaffolding to deflect, easing its withdrawal from the body lumen.

Described herein are certain exemplary embodiments. However, one skilled in the art that pertains to the present embodiments will understand that the principles of this disclosure can be extended easily with appropriate modifications to other applications.

What is claimed is:

1. A device for increasing a cross-sectional area of a body lumen, comprising a scaffolding with opposing first and second opposing tissue-engaging portions and at least one expansion member having a thickness, the scaffolding being configured to transition between a compressed configuration having a reduced distance between the first and second tissue-engaging portions and a deployed configuration having an increased distance between the first and second tissue-engaging portions, the first and second tissue-engaging portions having an increased surface area relative to the thickness of the expansion member, the first tissue-engaging portion being secured to a shaft at a first end of the shaft slidably secured within a housing, the shaft being positioned coaxially within the housing and having a driving element secured to a second end of the shaft for biasing the shaft outwards from the housing.

2. The device of claim 1, wherein each of the first and second tissue-engaging portions comprise a lateral plate.

3. The device of claim 2, wherein each of the first and second tissue-engaging portions further comprise an anchor.

4. The device of claim 1, wherein the at least one expansion member is telescoping.

5. The device of claim 1, wherein the at least one expansion member is a bi-directional expansion member and wherein the tissue-engaging portions are secured to opposing ends of the bi-directional expansion member.

6. The device of claim 1, wherein a pair of uni-directional expansion members are coupled in opposing directions and wherein each tissue-engaging portion is secured to one end of each uni-directional expansion member.

7. The device of claim 6, wherein the pair of uni-directional expansion members are coupled by a pivot, wherein the pivot is biased to align the uni-directional expansion members longitudinally but allows the uni-directional expansion members to deflect with respect to each other.

8. The device of claim 7, further comprising a tether secured to the pivot.

9. The device of claim 1, wherein at least a portion of the scaffolding is coated with an agent.

10. The device of claim 9, wherein the agent comprises an anti-encrustation agent.

11. The device of claim 1, further comprising an agent disposed within at least one reservoir formed in the scaffolding.

\* \* \* \* \*